(12) United States Patent
Nesbit et al.

(10) Patent No.: US 6,983,637 B2
(45) Date of Patent: Jan. 10, 2006

(54) APPARATUS AND METHOD FOR EVALUATING AND COMPARING GOLF CLUB HEAD DESIGNS BASED UPON MASS PROPERTIES AND IMPACT BEHAVIOR

(76) Inventors: Steven Manuel Nesbit, 790 Kesslersville Rd., Easton, PA (US) 18040; Francis Thomas Schodler, 1760 Madison Ave., Bethlehem, PA (US) 18017

( * ) Notice: Subject to any disclaimer, the term of this patent is extended or adjusted under 35 U.S.C. 154(b) by 73 days.

(21) Appl. No.: 10/619,372

(22) Filed: Jul. 14, 2003

(65) Prior Publication Data

US 2005/0011250 A1    Jan. 20, 2005

(51) Int. Cl.
*G01N 3/30*     (2006.01)
*G01N 3/52*     (2006.01)
(52) U.S. Cl. .................................. 73/12.02
(58) Field of Classification Search ............ 73/491, 73/12.04, 489, 12.02; 473/223, 221, 409, 473/345, 314, 291, 245, 324; 703/1
See application file for complete search history.

(56) References Cited

U.S. PATENT DOCUMENTS

| | | | |
|---|---|---|---|
| 5,351,953 A | 10/1994 | Mase | |
| 5,877,970 A | 3/1999 | Nesbit | |
| 6,041,651 A | * 3/2000 | Naruo et al. | .................. 73/491 |
| 6,045,455 A | 4/2000 | Kosmatka | |
| 6,186,905 B1 | 2/2001 | Kosmatka | |
| 6,425,832 B2 | 7/2002 | Cackett | |
| 6,506,124 B1 | 1/2003 | Manwaring | |

* cited by examiner

*Primary Examiner*—Max Noori
*Assistant Examiner*—Octavia Davis

(57) ABSTRACT

The golf club head evaluation system provides two methods for evaluating and comparing various club head designs. Method one is a data acquisition apparatus that captures, processes, and displays the bending and torsional deflections and accelerations of a golf club shaft in response to impact loads applied to an attached golf club head. Method two provides a graphical method for comparing the inertia properties of golf club heads based upon equivalent inertia ellipsoids. The apparatus contains an instrumented shaft that is supported in a cantilevered position. Golf club heads of various configurations are attached to the end of the shaft. Their graphical images and mass properties are input to the computer. From the mass property data, an ellipsoid is created with equivalent mass properties. The club head graphical images are presented to the user with superimposed equivalent inertia ellipsoids that facilitate direct comparison of mass properties among different club heads, and for determining desired impact locations. Magnitude and location variable impact loads are applied to the club head by a falling steel ball. The shaft is attached to a rigid steel frame and instrumented with strain gauges configured in a Wheatstone half-bridge arrangement, and with a three-axis accelerometer. The data acquisition system is triggered by the falling ball passing through a light beam. A strain gauge data acquisition board in a central processing unit records strain information. An oscilloscope records data from the accelerometer. A set of computer programs collect strain gauge and accelerometer readings from the shaft, processes and stores the data, and plots the data on a computer screen. Plots include impact induced deflections and accelerations for central and eccentric impact loads, measured in different angular and linear directions. From the experimental data and the equivalent inertia ellipsoids, and the relative merits of various club head designs can be determined and compared.

1 Claim, 15 Drawing Sheets

APPARATUS AND METHOD FOR EVALUATING AND COMPARING GOLF CLUB HEAD DESIGNS BASED UPON MASS PROPERTIES AND IMPACT BEHAVIOR

This invention, relates to an apparatus and method for comparing golf club head designs based upon their mass properties and impact behavior. More particularly, this invention relates to an apparatus and method for comparing golf club head designs graphically through equivalent inertia ellipsoids, and quantitatively through measuring the deflection and acceleration impact behavior of various golf club head configurations.

As is known, various techniques have been employed for measuring the mass properties, specifically the mass, mass center location, and inertia tensor components of golf club heads. These data have been used to make relative comparisons among different club head configurations. It is also well known that the mass properties of the club head have an influence on the golfer, the golf swing, the impact between the ball and the club head, and ultimately the distance and accuracy of the golf shot. Mass property data is also useful for club designers and manufacturers when configuring and designing golf club equipment.

It is well known that club head mass properties affect various aspects of the golf shot. However, the specific relationships among the different mass properties and the outcome of the golf shot have not been quantified, and are only partially understood qualitatively. In any case, designers do configure club head geometry to effect the overall mass properties. Examples of club designers affecting the mass properties of the club head, more specifically the inertia tensor properties are evident in the oversized drivers and perimeter-weighted irons. This purposeful manipulation of club head mass properties is done to increase the size of the club head 'sweet spot'. In other words, the club head will be less responsive or more forgiving to an impact not coinciding with the club head mass center. Designers do have analytical tools available to configure a cub head to meet pre-specified mass properties. Unfortunately designers do not have the ability to directly determine the effects of club head mass manipulation on the overall mass properties. Nor do they have the ability to make quick and direct visual comparisons among various club head geometries in terms of mass properties. Nor do they have the ability to predict the impact behavior of golf clubs with various club heads attached. In general new club head configurations are proposed then presented to the golfing public who determines through trial-and-error the merits of a new design. Thus club head design is more of an art than a science at this time.

Golf club designers have a difficult time in qualitatively and quantitatively evaluating the six values of the inertia tensor as they manipulate the mass of a club head during the design process. Further, mass moment of inertia values tend to be more of an abstraction as opposed to weight and mass center location. Thus visual evaluation and comparison of club heads based upon inertia tensor values is not possible.

However, it has not been known that any attempt has been made to configure a device that determines the impact behavior of a golf club head in terms of measured deflections and accelerations, for various types of impacts such as central, and heel-toe and top-bottom miss hits. It has not been known that any attempt has been made to provide a quick and easy graphical method for directly comparing the mass properties of various club head designs. It has not been known that any attempt has been made to create a system for comparing golf club head designs based upon mass properties and impact behavior.

Accordingly, it is an objective of this invention to provide an apparatus to accurately measure the deflection impact behavior of various golf club heads.

It is another objective of this invention to provide an apparatus to accurately measure the acceleration impact behavior of various golf club heads.

It is another objective of this invention to use the deflection and acceleration impact behavior to make direct comparisons among different golf club head designs.

It is another objective of this invention to provide a convenient means to make qualitative comparisons of the inertia characteristics of various club heads.

It is another objective of this invention to provide a method and apparatus to assist in the golf club design process.

It is another objective of this invention that the system be easy to operate, and provide quick and meaningful data and graphical information.

It is another objective of this invention to be able to evaluate golf equipment based upon their mass and inertia properties, and impact behavior.

It is another objective of this invention to be able to analyze and compare golf equipment.

Briefly, the invention provides an apparatus and method for evaluating and comparing club head designs based upon their impact behavior and mass and inertia properties. The apparatus for measuring various impact behaviors comprises an instrumented shaft upon which a golf club head to be evaluated is mounted. The shaft is designed and instrumented to not only react to and record deflection response, but to react to and record acceleration response as well. To this end, the instrumented shaft is attached to a rigid steel test frame in a cantilevered manner. The steel shaft is able to accept various golf club heads. The rig also supports a vertical tube through which a steel impacting ball is dropped and guided. The tube and impact ball can be adjusted in several ways above the golf club head. The height of the ball in the tube is adjustable so that the ball can impact the club head at various velocities. The tube can also be adjusted laterally so that the ball can be made to impact the head at various locations relative to its mass center.

Impact induced shaft deflections are measured with strain gauges. Half-bridge configurations of eight strain gauge sets (eight sets of two gauges each) located in various positions and orientations are used to measure both torsional and bending deflections. Three sets of strain gauges are used to measure the deflection in the swing plane (the plane in which the club is swung). These sets of gauges are mounted to the handle, midpoint, and end of the shaft, with each pair of gauges located on the top and bottom of the shaft and oriented with the long axis of the shaft. Three additional sets of strain gauges are used to measure the deflection in the pitch plane (the plane perpendicular to the swing plane and containing the shaft). These sets of strain gauges are also mounted to the handle, midpoint, and end of the shaft, with each pair of gauges located on opposite sides of the shaft and oriented with the long axis of the shaft. Another two sets of strain gauges are used to measure the torsional deflection of the shaft. These strain gauges are located at one third and two thirds down the length of the shaft, with each pair of gauges located on opposite sides of the shaft. These gauges are oriented at an angle of 45 degrees relative to the long axis of the shaft, and 90 degrees relative to each other in a set. An eight-channel, PC mounted strain gauge board is used to record the strain gauge signals. The data acquisition system used on this invention has an acquisition rate of 180 Hz per channel. An optical sensor is used trigger/activate the data acquisition system.

The accelerations, which are an indication of transmitted forces and torques resulting from the steel ball impacting the club head, are measured with an orthogonal triad of uniaxial accelerometers. This accelerometer unit can be positioned at several locations and orientations along the shaft via a series of threaded holes along the shaft length. These holes are on the top, bottom, and sides of the shaft. To measure the angular accelerations, an indication of transmitted torques, the accelerometer unit is mounted to a rigid torsion arm which is then attached securely to the shaft in a perpendicular orientation via the same mounting holes. The torsion arm with the accelerometer unit is placed on the underside of the shaft to isolate it from the predominate bending forces so to only measure torsional accelerations. A digital oscilloscope with a bandwidth of 100 MHz is used to record and store the accelerometer signals. This data acquisition function is front edge triggered by the oscilloscope, or with the optical trigger. The data is dumped to the system PC for processing, display, and storage.

The method for evaluating and comparing the mass and inertia properties of club heads consists of software for displaying graphical images club heads, and numerical algorithms for configuring equivalent inertia ellipsoids. The club head to be evaluated and/or compared is displayed graphically on the system computer using any one of several CAD software packages such as AutoCAD. The multiple graphical are presented include the location of the mass center, and the orientation of the principal inertia axes. This information is provided so to properly locate the desired impact. The user also enters the mass properties of the cub head into the computer. These properties include the club head mass (or weight), the three coordinates of the mass center location, and the six independent components of the inertia tensor. From the inertia tensor information, the principal inertia values, and principal orientations are determined using standard methods of mechanics. The club head mass and principal inertia values are equated to the formulas for determining the principal inertias for a solid ellipsoid so to configure a solid ellipsoid with the same mass and principal inertia values as the club head. This equivalent "inertia ellipsoid" is overlaid on the graphical image of the club head with coincident mass centers and principal orientations. The inertia ellipsoid provides a graphical means for qualitatively evaluating the mass properties of the club head, and indirectly, the impact behavior of the club head. More significantly however, the equivalent inertia ellipsoid provides a means for making direct comparisons of the mass and inertia properties among various club head designs. It also allows for comparative mass property evaluation of individual club head design modifications/iterations. These comparisons are not possible using geometry alone.

These and other objects and advantages of the invention will become more apparent from the following description taken in conjunction with the accompanying drawings wherein.

Figure 1:
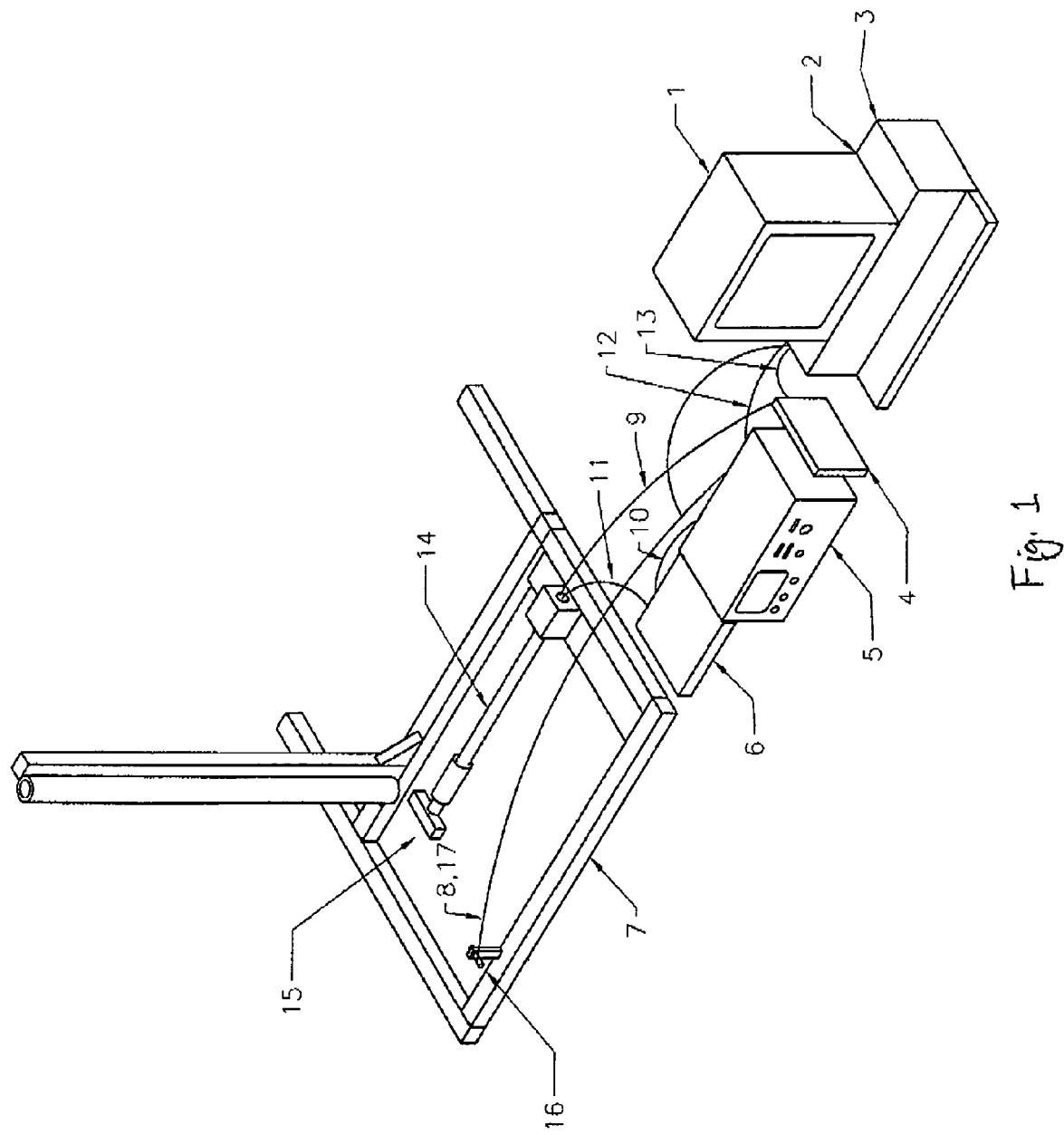
FIG. 1 illustrates an apparatus and method for evaluating and comparing golf club head designs based upon mass properties and impact behavior employing a data acquisition system and analytical methods in accordance with the invention.
Figure 2:
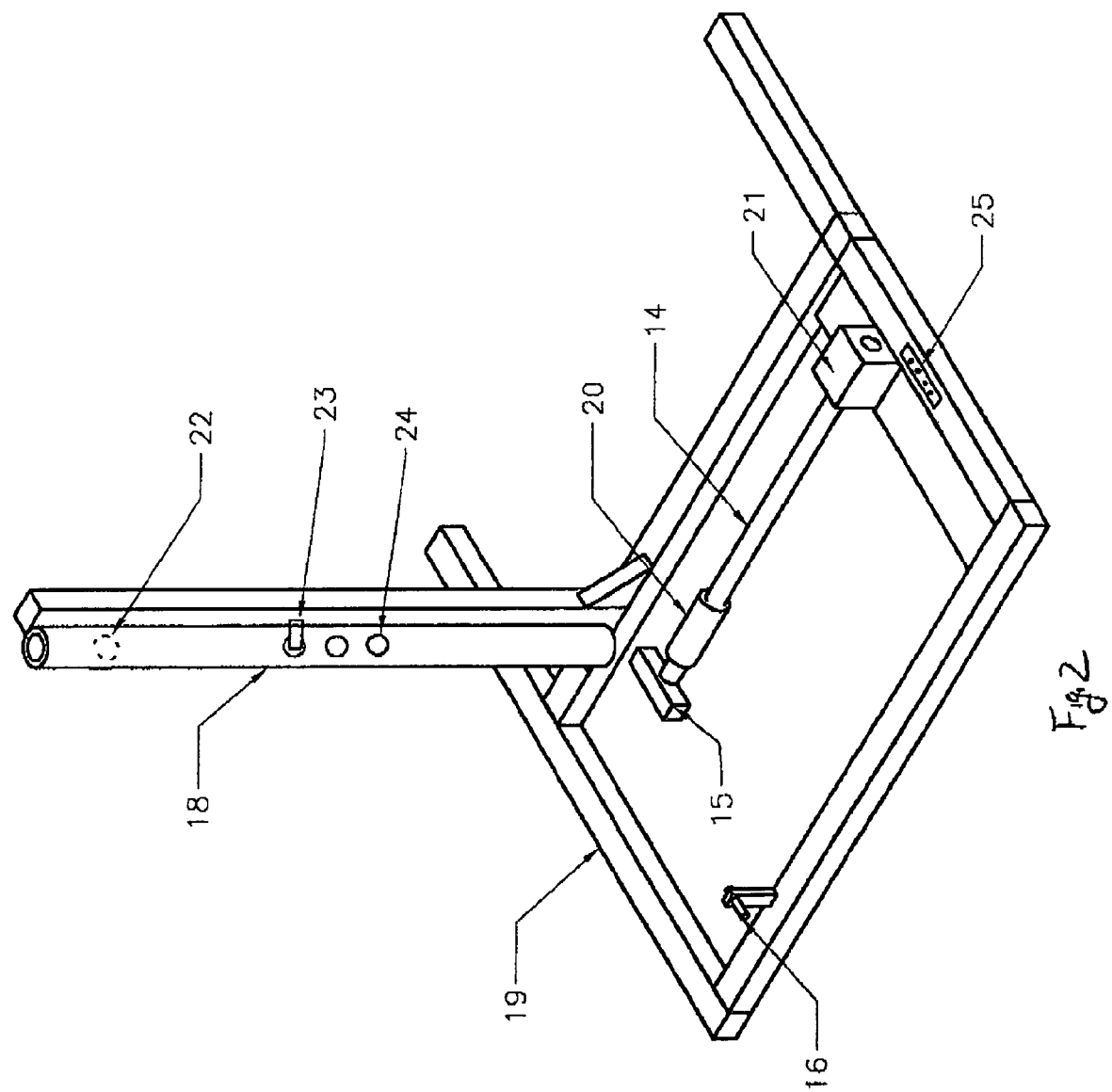
FIG. 2 illustrates a more detailed view of the test apparatus of FIG. 1.
Figure 3:
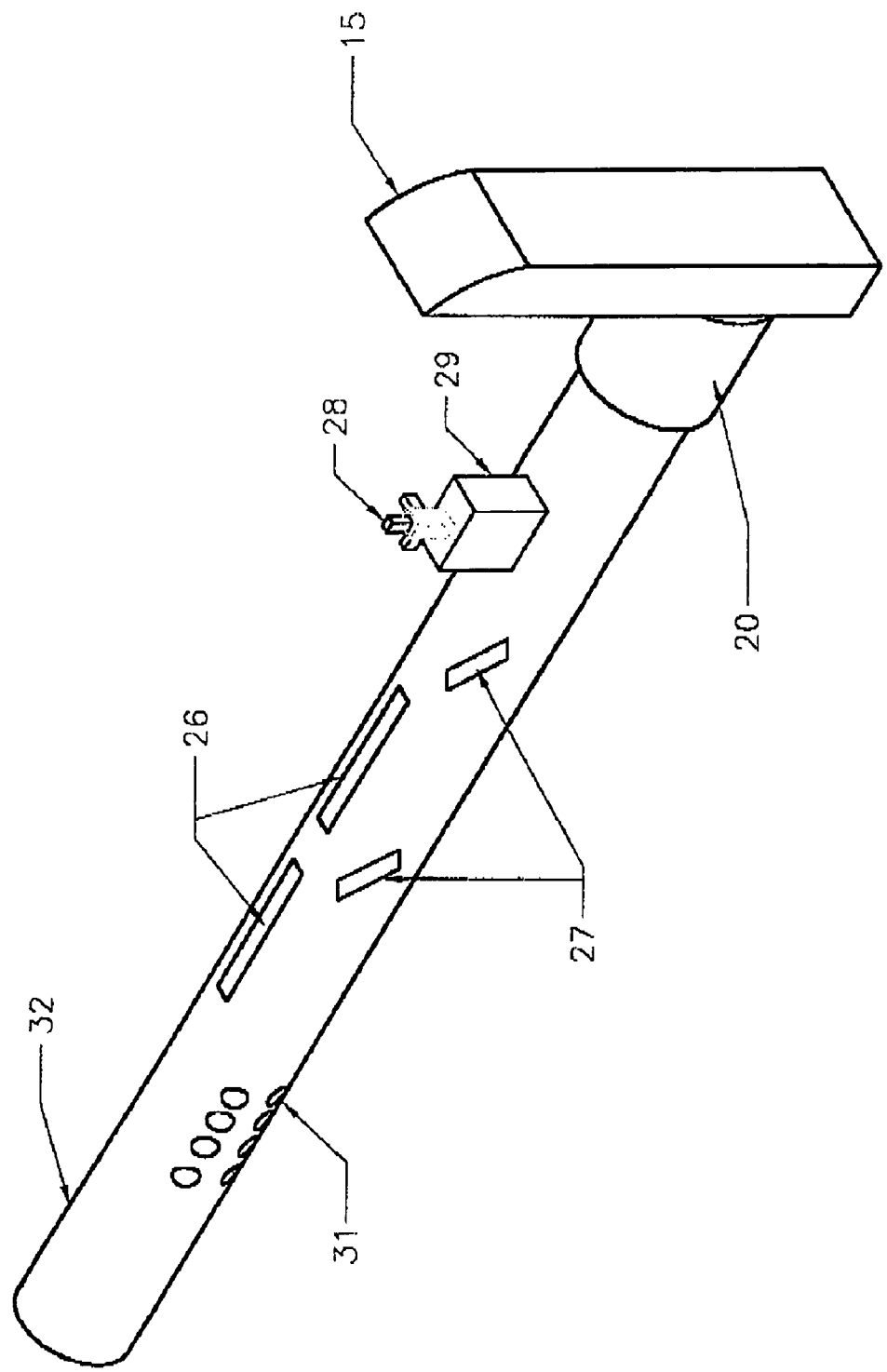
FIG. 3 illustrates a more detailed view of the instrumented club of FIG. 2.
Figure 4:
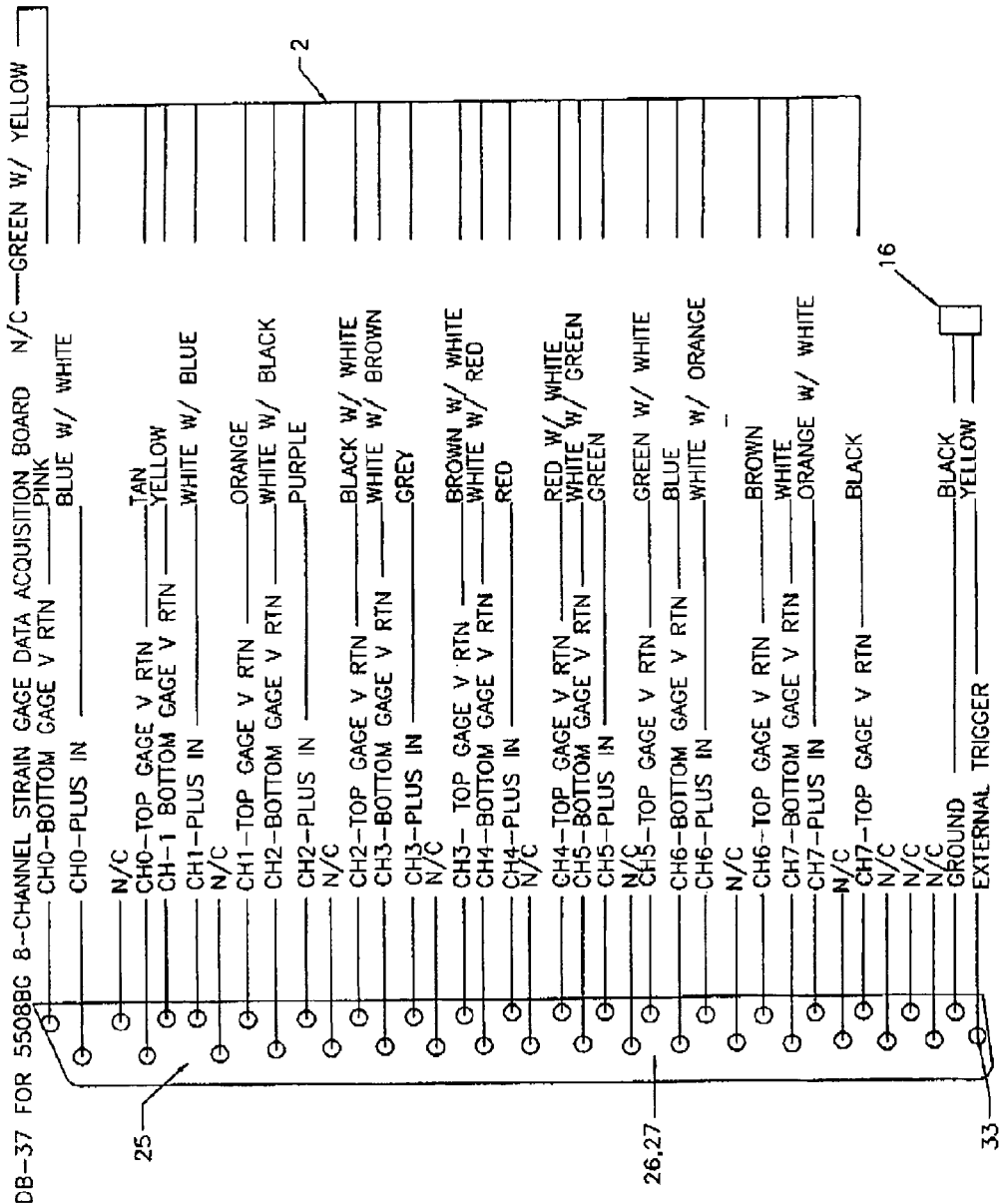
Figure 5:
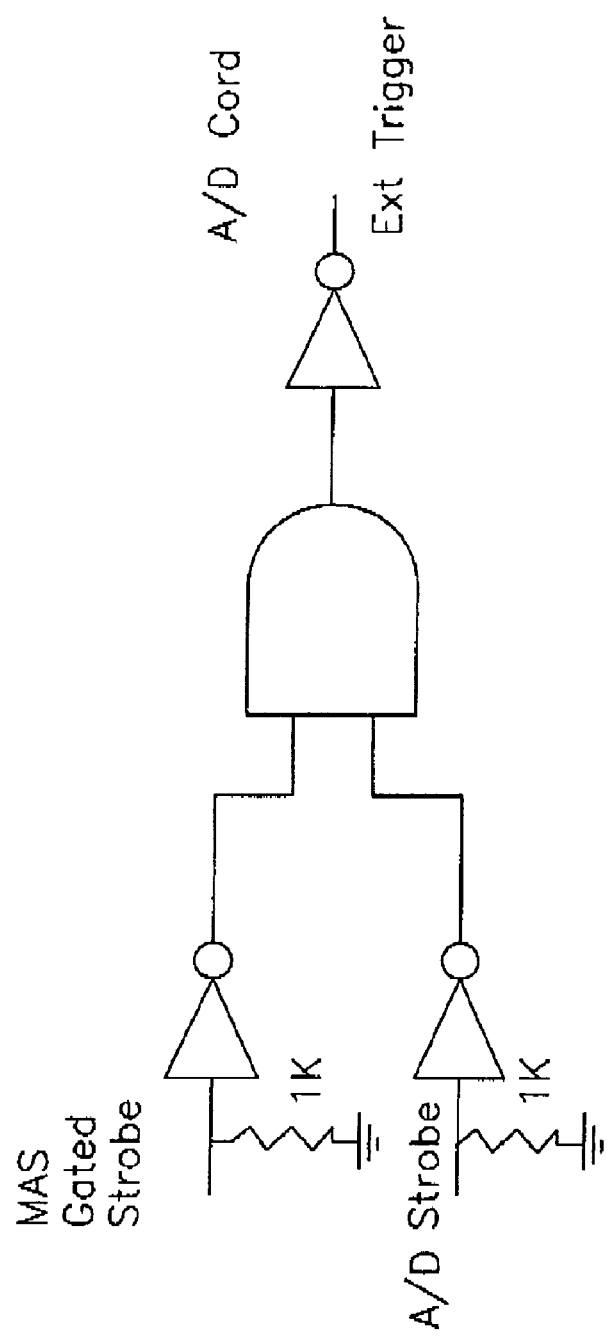
Figure 6A:
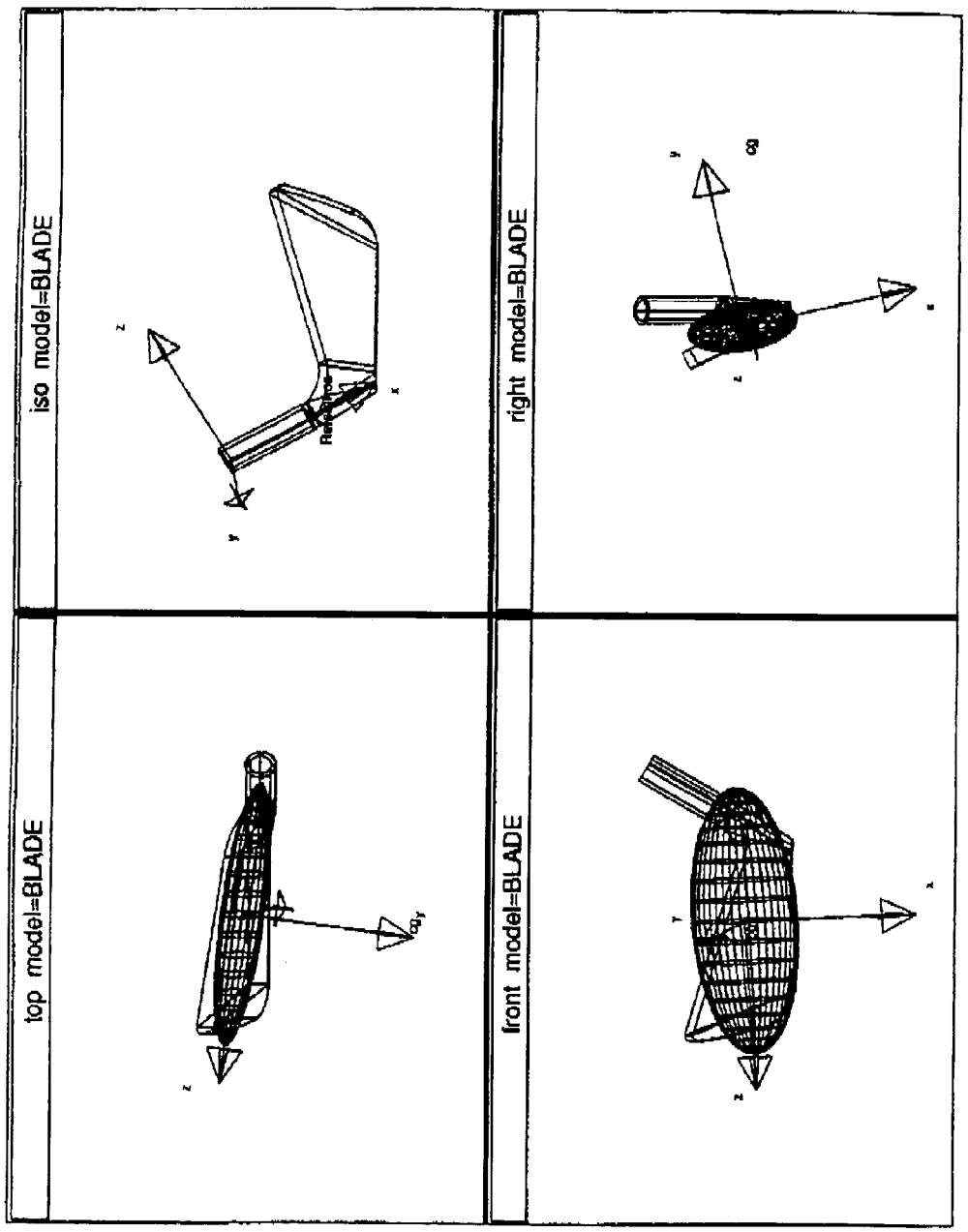
Figure 6B:
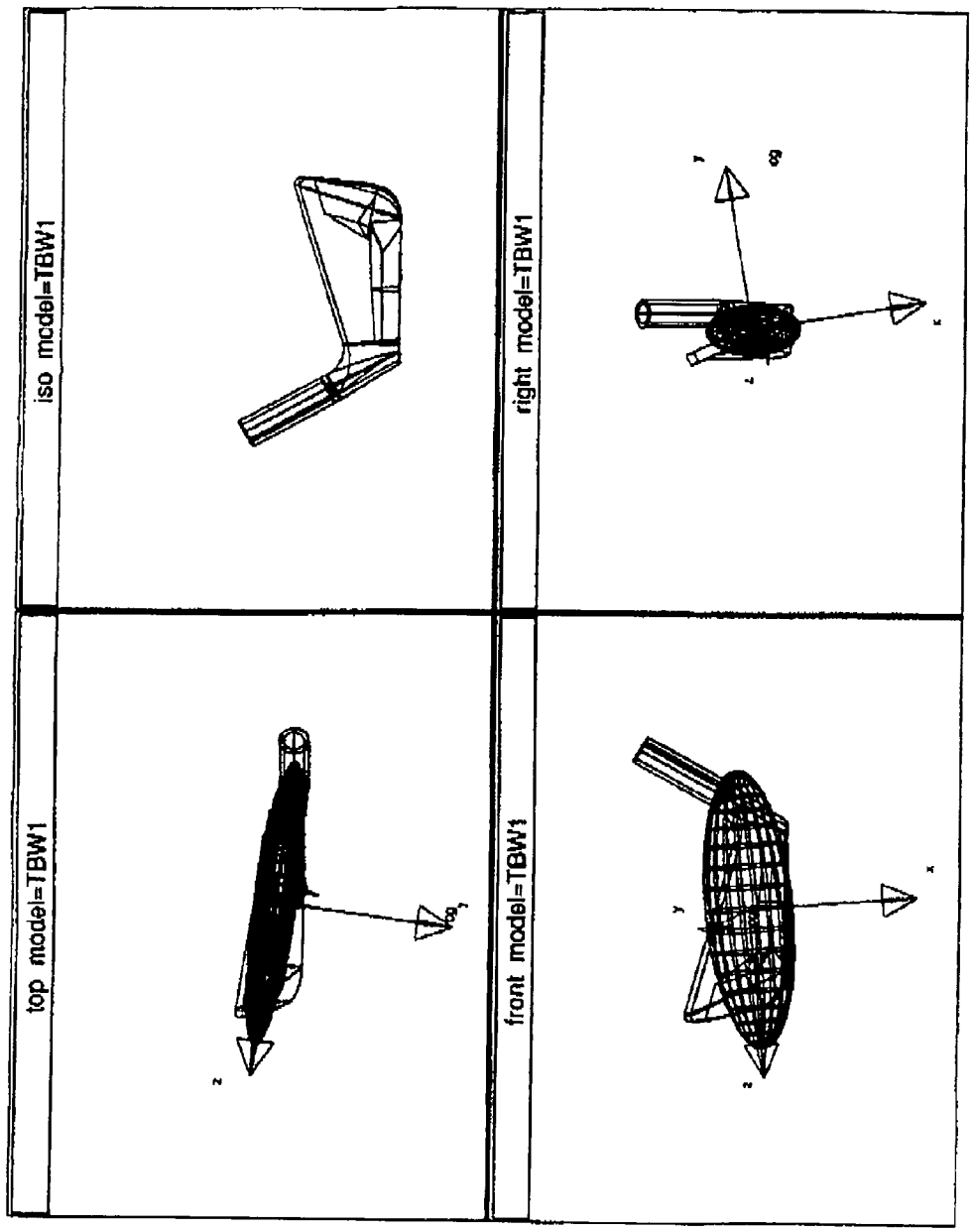
Figure 6C:
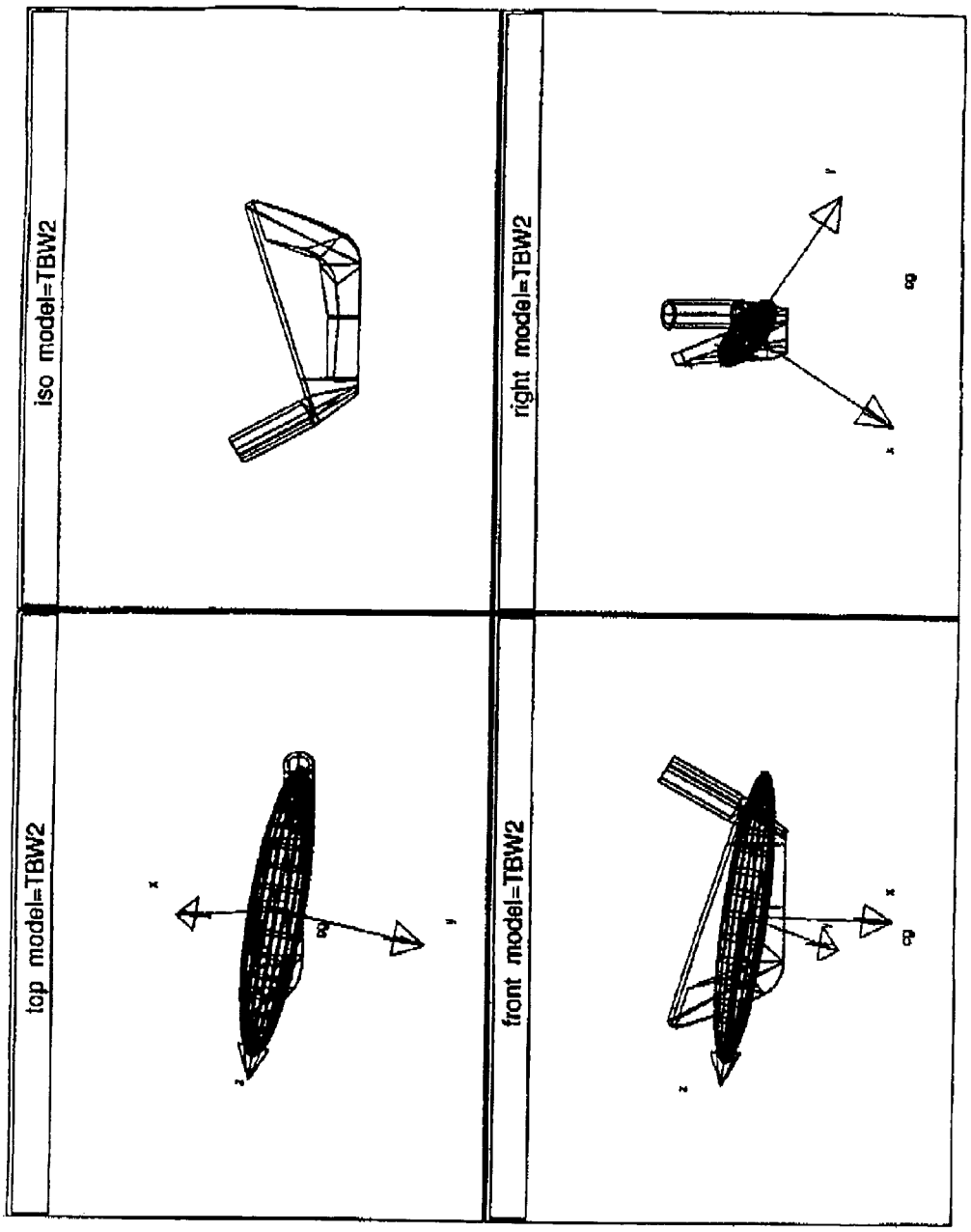
Figure 6D:
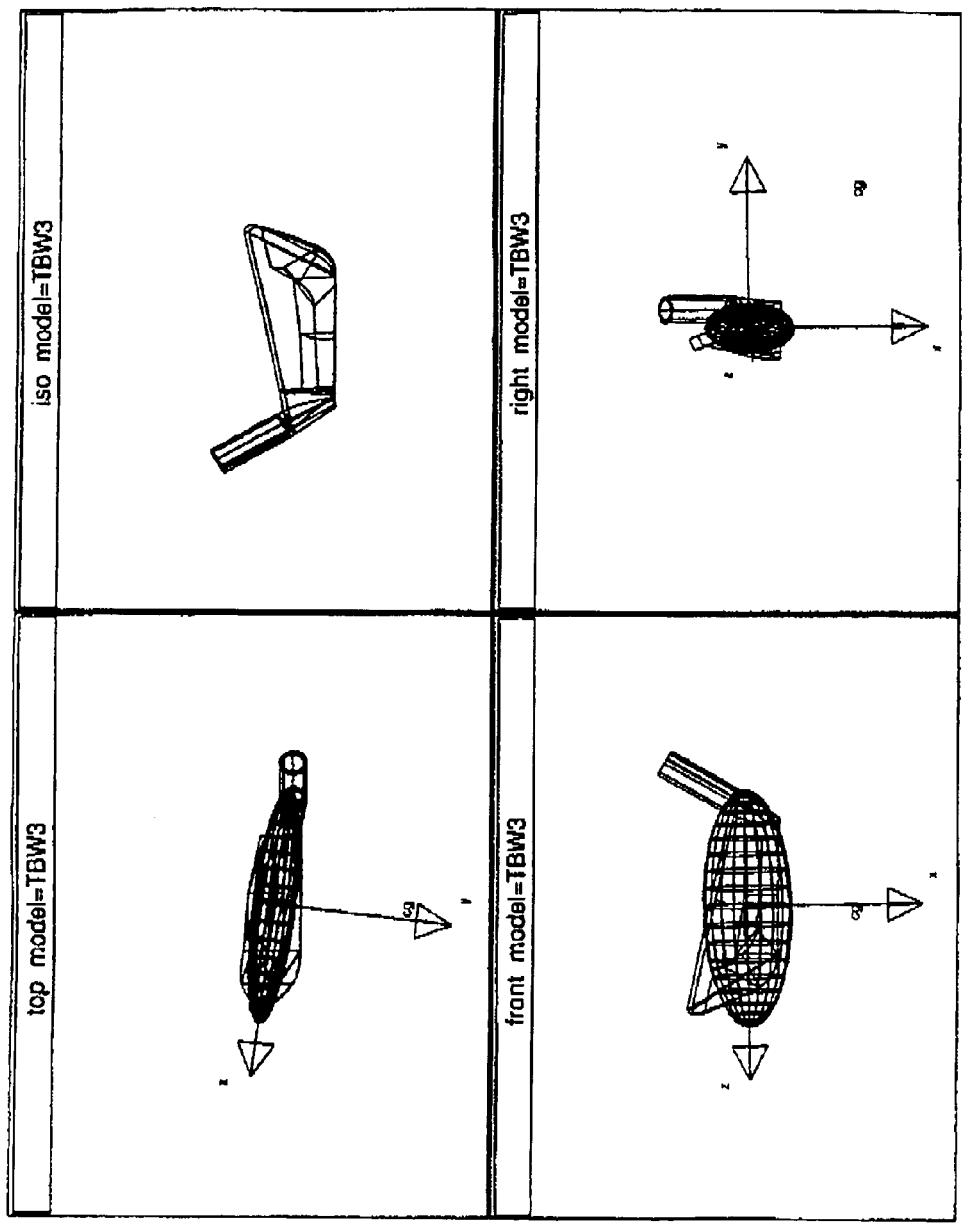
Figure 6E:
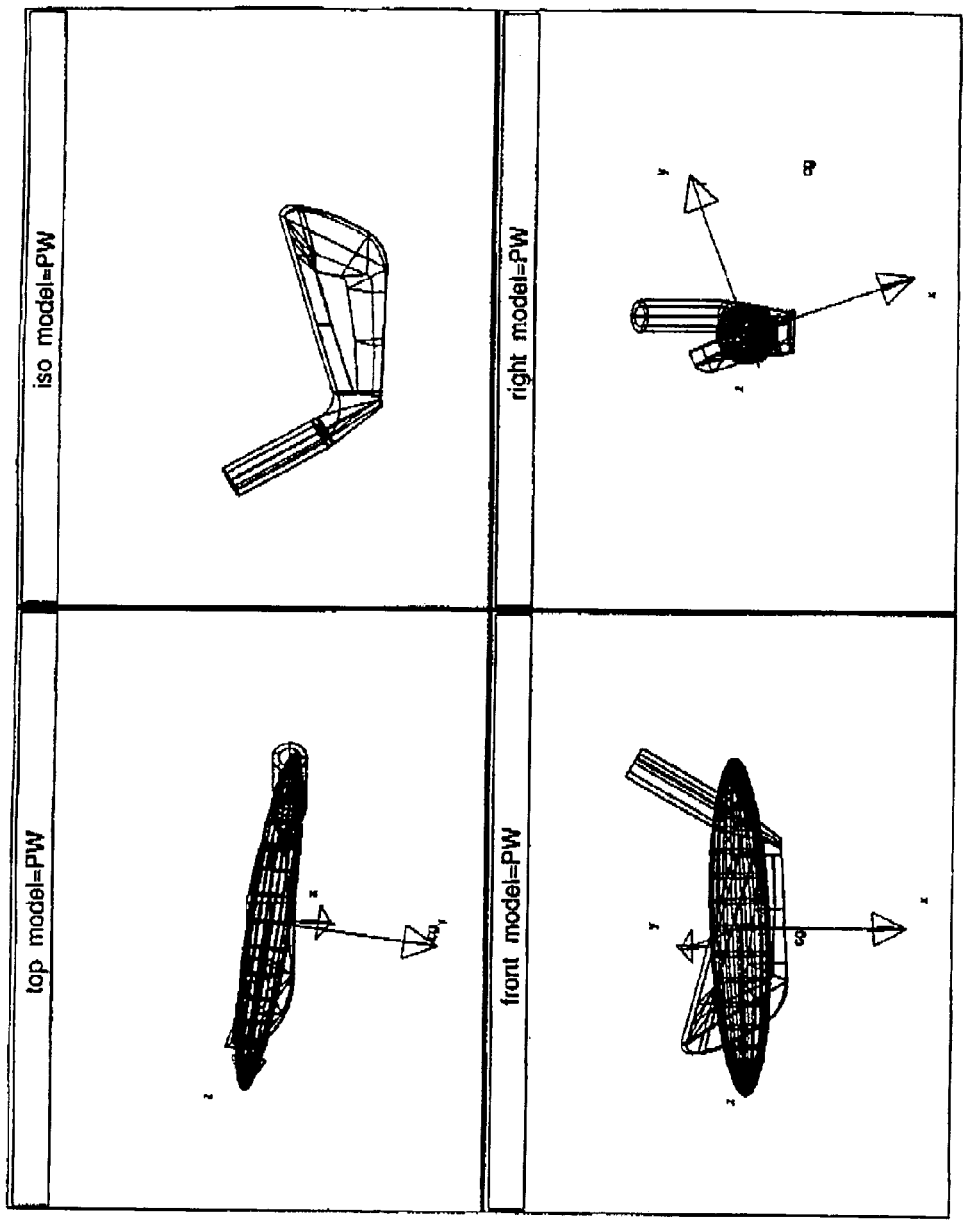
Figure 6F:
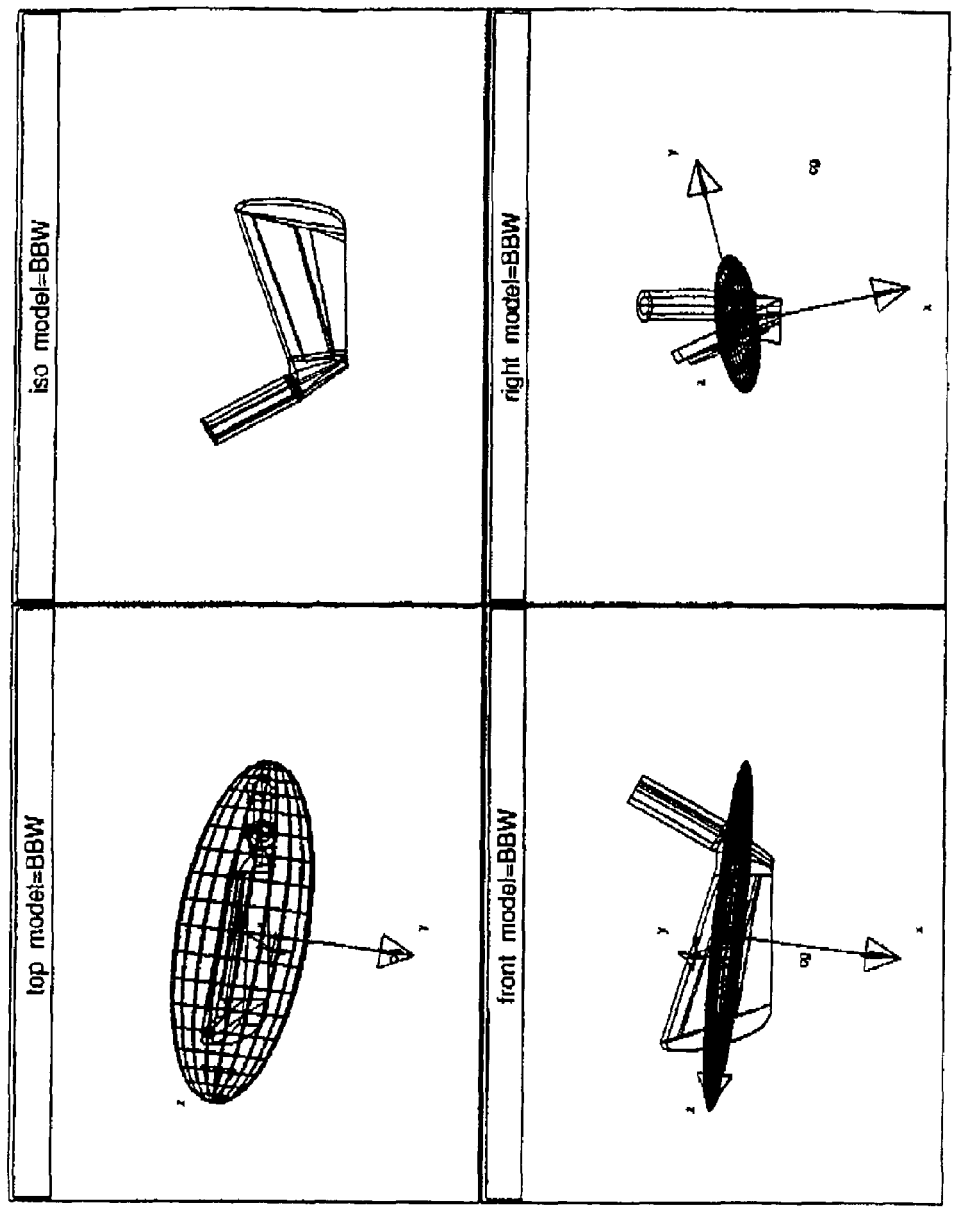
Figure 7:
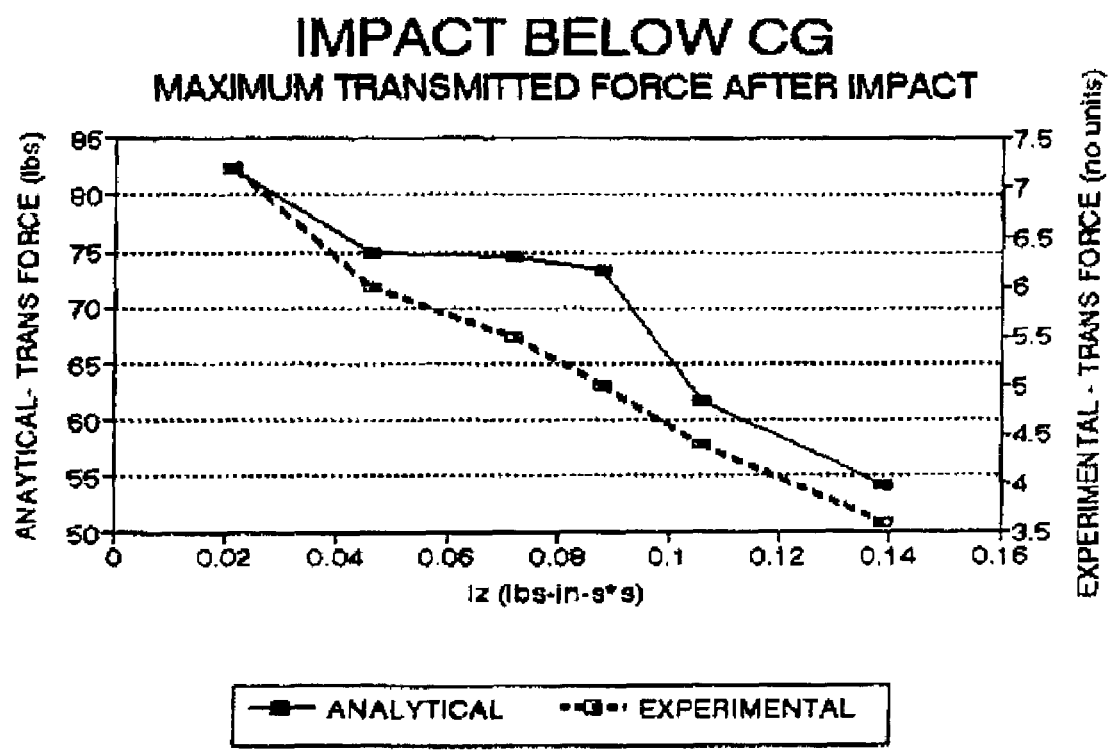
Figure 8:
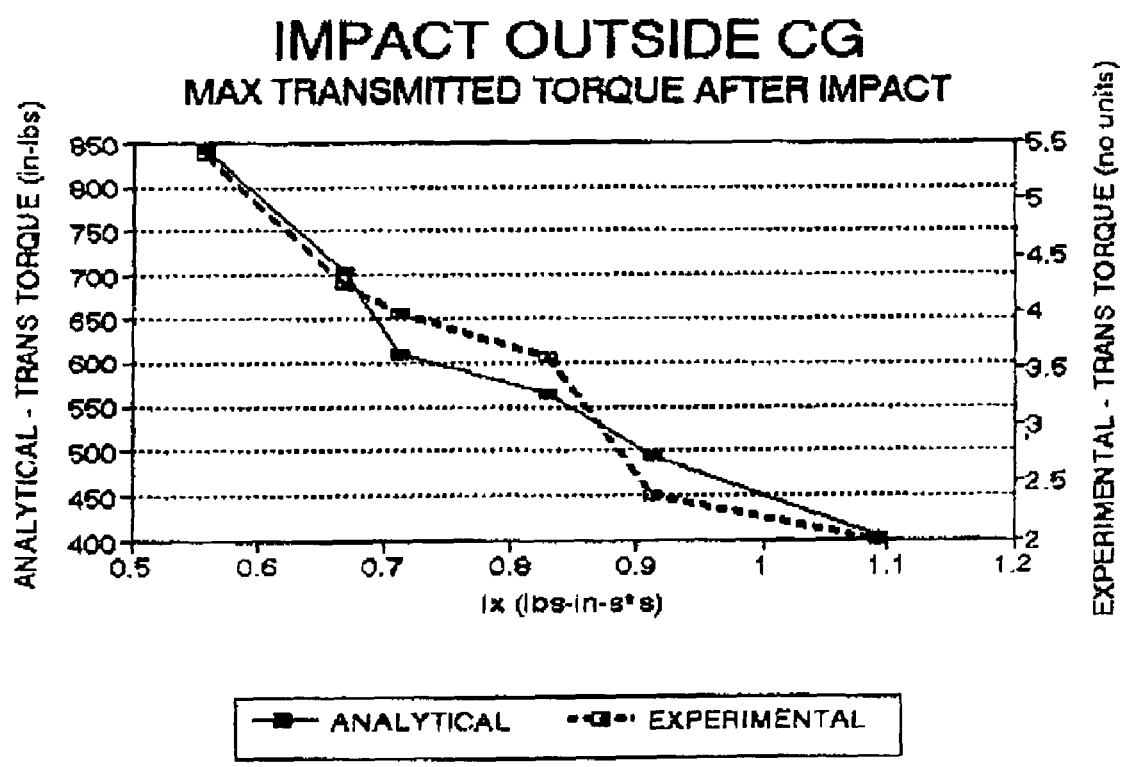
Figure 9:
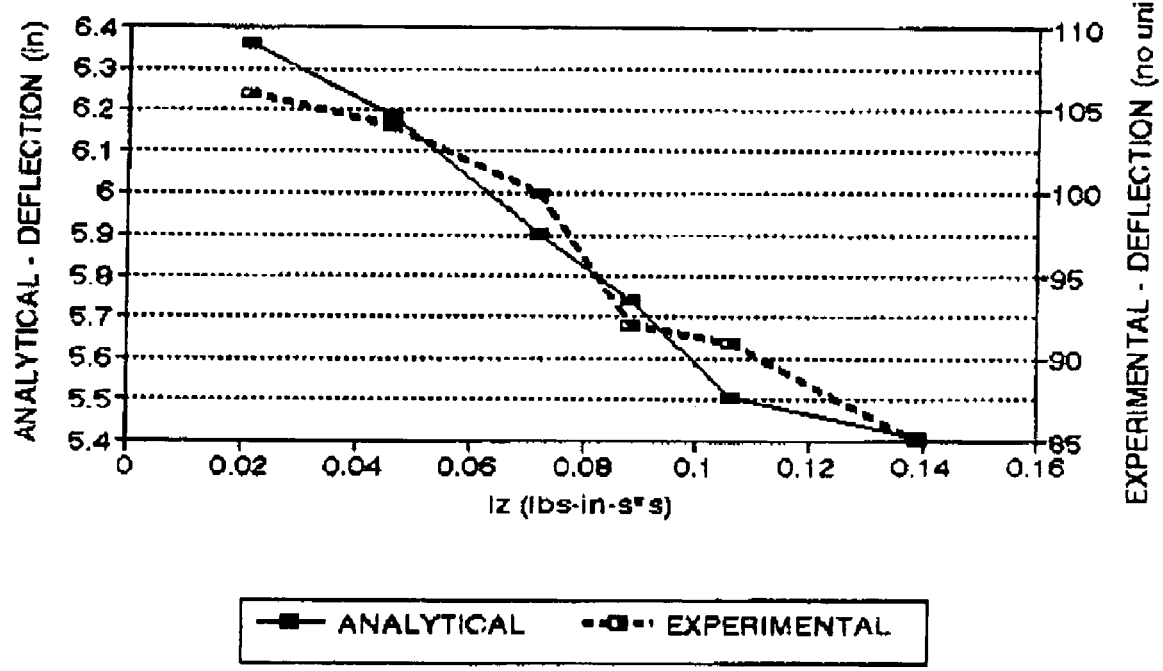
Figure 10:
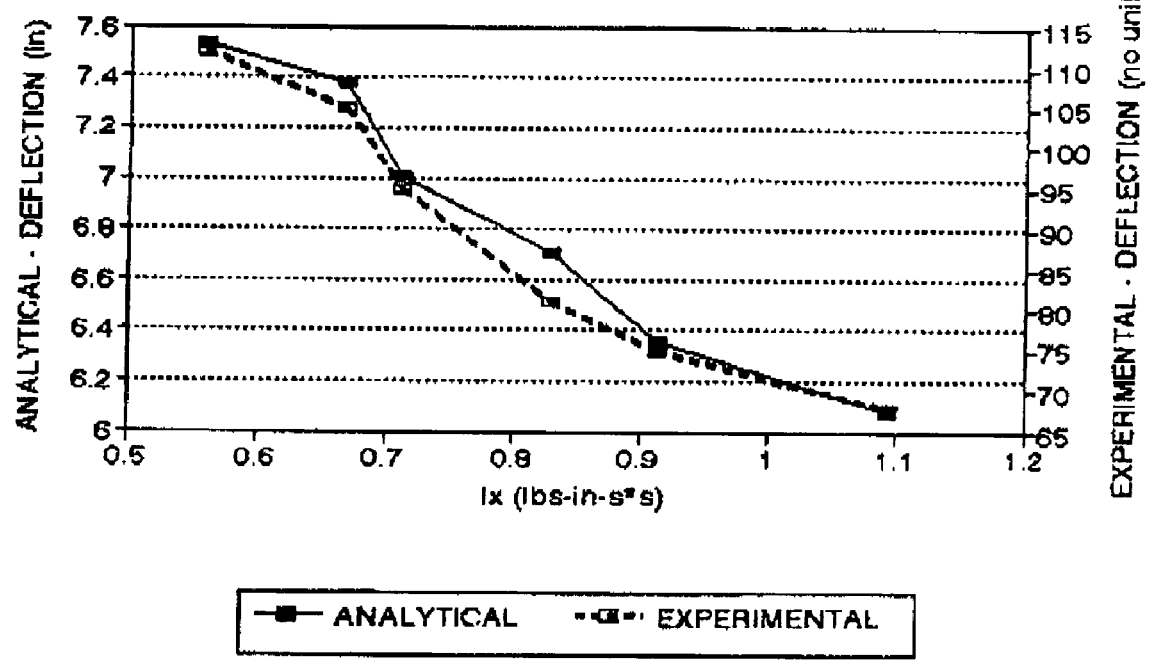

FIG. 4 schematically illustrates partial connections between the shaft of FIG. 3 and a data acquisition board of a central processing unit in accordance with the invention;

FIG. 5 illustrates a schematic diagram of the circuitry and components used in the synchronous trigger unit of FIG. 2;

FIGS. 6a through 6f illustrate views of various club head designs of five irons with superimposed principal inertia axes and equivalent inertia ellipsoid in accordance with the invention;

FIG. 7 graphically illustrates the measured transmitted force (acceleration data) for an impact below the mass center, as a function of the relevant principal inertia component, as determined by the accelerometer portion of the data acquisition system, with the data compared to analytical predictions;

FIG. 8 graphically illustrates the measured transmitted torque (acceleration data) for an impact outside the mass center, as a function of the relevant principal inertia component, as determined by the accelerometer portion of the data acquisition system, with the data compared to analytical predictions;

FIG. 9 graphically illustrates the measured deflection for an impact below the mass center, as a function of the relevant principal inertia component, as determined by the strain gage portion of the data acquisition system, with the data compared to analytical predictions;

FIG. 10 graphically illustrates the measured deflection for an impact outside the mass center, as a function of the relevant principal inertia component, as determined by the strain gage portion of the data acquisition system, with the data compared to analytical predictions;

Briefly, the apparatus is constructed so as to take various acceleration and deflection measurements of the instrumented shaft and to develop computer plots of the collected and processed data. Referring to FIG. 1, the system for evaluating, comparing, and determining the effects of golf club head mass properties on club behavior employing a rigid test frame 7, instrumented shaft 14, sensor amplifiers 4, 6, oscilloscope or the like 5, and a central processing unit 3. The central processing unit contains the computer screen monitor 1 for displaying test data and club head/ellipsoid models, and the strain gage data acquisition board 2. The instrumented shaft 14, which is attached to the rigid test frame 7, has strain gages and accelerometers mounted on as described below. The club head to be evaluated 15, is mounted to the free end of the instrumented shaft 14. The accelerometer signals go to an amplifier 6, then to an oscilloscope 5, for processing, display, and temporary storage. Accelerometer data can be transferred to the central processing unit 3, for further processing, long term storage, and comparison purposes. The accelerometers, amplifier, oscilloscope, and central processing units are, connected via suitable lines 10, 11, and 12. The strain gage signals go to a stain box amplifier 4, then to the strain gage data acquisition board 2, inside the central processing unit 3. The strain gages, strain box amplifier, stain gage data acquisition board, and central processing units are connected via suitable lines 9, and 13. Data acquisition can be initiated with the synchronous trigger 16, which is connected via suitable lines 8, 17, to the oscilloscope 5 (accelerometer data acquisition), and to the central processing unit 3 (strain gage data acquisition).

The central processing unit 3, also contains the method for evaluating and comparing golf club head designs based upon their mass properties. As such, the central processing unit contains programs for displaying several views of the graphical image of the club head being evaluated; for determining the equivalent inertia ellipsoid based upon the user input of the club head mass properties; and for displaying the ellipsoid superimposed on the club head images. This method is described in detail in the Theory of Operation section that follows.

Referring to FIG. 2, the rigid test frame is constructed of rectangular shaped hollow tubes 19, with two sets of parallel sides, one of which has extended legs for stability, and a vertical leg to support the tube 18 through which the impacting ball 22, is dropped and guided. All of the frame rails are made of a suitable material, i.e. steel. All frame rails are fastened to each other by use of welds. The impacting ball 22, is height positioned and released with pin 23. The height of the ball is adjustable via holes 24. The tube can be located in several different locations above the golf club head 15. Because the tube can be laterally adjusted with respect to the face of the golf club head, it enables the ball to impact the head in various locations. The construction of the apparatus is such that downward impact force created by the ball striking the golf club head causes accelerations, forces, torques, and deflections in the instrumented shaft 14. The instrument shaft 14, is attached to the frame in a cantilever manner via suitable mounting hardware 21. The club head to be tested 15, is mounted at the free end of the instrumented shaft via universal type mounting hardware 20. The synchronous trigger. 16, is attached to the frame and interfaced as shown in FIG. 1. A multi-pin terminal strip 25, is attached to the frame to serve as an interface between the delicate wire connections of the instrumented shaft, and the more robust wired connections of the data acquisition equipment.

A detailed drawing of the instrumented shaft assembly is shown in FIG. 3. The shaft assembly consists of a solid shaft 32, strain gages 26, 27, accelerometer triad 28, torsion arm mounting apparatus for the accelerometers 29, and associated mounting holes 31, mounting apparatus for the club heads 20, and the club head to be tested 15. The instrumentation includes multiple sets (not all shown of parallel mounted strain gages 26, for measuring bending deflections at various locations along the shaft, and multiple sets (not all shown) of diagonally mounted strain gages 27, for measuring torsional deflections at various locations along the shaft. In a typically half-bridge arrangement, there will be strain gages mounted diagonally opposite the gages shown in the figure in the appropriate direction to configure as a half-bridge. This gauge configuration has two distinct benefits. One, the gauge configuration doubles the magnitude of the reading relative to a single gauge configuration. Two, the configuration ignores deflections associated with temperature changes.

The shaft instrumentation also includes a triad of orthogonally oriented uniaxial accelerometers 28, mounted to, a torsion arm, 29, and attachable to the shaft at a variety of locations and orientations via the mounting holes 31. The mounting torsion arm allows for amplification of torsional accelerations in different directions. The series of mounting holes allows for accelerometer measurements at different locations and orientations along the shaft, which among other factors affects sensitivity, magnitude, and direction. A digital oscilloscope 5 (FIG. 1), with a bandwidth of 100 MHz was used to capture the accelerometer signals. The digital oscilloscope is interfaced to the central processing unit 3 (FIG. 1). The central processing unit, contains programs to run the accelerometer data acquisition system, and capture, process, store, and plot the accelerometer data on the display 1 (FIG. 1).

Referring again to FIG. 1, an eight-channel, PC mounted strain gauge board 2; records the strain gauge signals. The data acquisition system used on this invention had an acquisition rate of 180 Hz per channel. Each channel on the board represents one Wheatstone bridge. All channels have the following configuration; two strain gauges on the shaft make up one-half of a Wheatstone bridge circuit; two on-board high-precision fixed resistors complete the bridge; the board supplies 5 VDC to the bridge. The strain 1 gauge data acquisition board is provided with a plurality of analog/digital converters (not shown) for transforming the analog voltage signals from the strain gauges into discrete binary numbers at a predetermined time rate. The processing unit 3, stores the binary number data received from the strain gauge data acquisition board. The processing unit contains programs to zero the unloaded strain gages, calibrate the strain data to shaft deflections, run the strain gage data acquisition system, capture and store the strain gage data, convert the stored binary numbers to shaft deflections, and plot the results on the display 1.

FIG. 4 schematically illustrates the partial connections between the strain gages 26, 27, of the instrumented shaft, the synchronous trigger 16, and the data acquisition board, of the central processing unit computer. (Note that the numbers in this figure represent connections to, and data flow through the components.) The wired connections from the strain gages are securely connected to a terminal strip 25. A wire ribbon 33, completes the connection from the terminal strip to the data acquisition board.

FIG. 5 illustrates a schematic diagram of the circuitry and components used in the synchronous trigger unit 16, of FIG. 2. The trigger can be a light beam, ultrasonic sensor, or any similar device that is activated by the impacting ball passing by or through the sensor. The trigger initiates data acquisition of the strain gages and/or the accelerometers. Data acquisition may also be initiated by computer keyboard entry, or front end data collection.

Theory of Operation

The basis for operation of the deflection measurement data acquisition portion of the invention is the relationships between a particular point load and the resulting linear and torsional deflections. For the linear case, the relationship between a point load F, and the deflection Y, is given by:

$$Y = -FL^3/(3*E*I) \qquad (1)$$

where L is the length of the beam from the support to the point of application of the load, E is the modulus of elasticity of the material of the beam (instrumented shaft), and I is the area moment of inertia of the cross section of the beam. Therefore, from equation (1), as long as the loading does not cause stress in the beam material to exceed the elastic limit, the deflection and loadings are linearly related.

For the torsional deflections, the relationship between a torque load T, and the angular deflection Theta, for a uniform straight member is given by:

$$Theta = T*L/(G*J) \qquad (2)$$

where L is the length of the member from the support to the point of application of the torque, G is the modulus of rigidity of the material of the member (instrumented shaft), and J is the polar area moment of inertia of the cross section of the beam. Therefore, from equation (2), as long as the loading does not cause the stress in the member material to exceed the elastic limit, the torsional deflections and loadings are linearly related.

These two deflections occur simultaneously on the instrumented golf shaft with club head attached since the application of the primary loading (impact load) is on the club face which is offset relative to the long axis of the golf shaft. The force F is the direct result of the impact. The torque T is the result of the impact force F applied an offset distance from the long axis of the shaft with the torque equal to F time this distance. The theory of superposition and the logical orientation of the strain gage pairs allows for the isolation and thus direct measurement of the linear and torsional deflections separately.

Strain gages mounted parallel to the long axis of the shaft and configured in a Wheatstone half-bridge circuit, measure the linear deflections of the shaft as a proportional change in voltage (analog signal). The analog-digital converter on the strain gage data acquisition board transforms analog voltages obtained from the Wheatstone bridge into discrete numbers (digital signal), and calibration equations relate the binary numbers to beam linear deflections. In a similar manner, strain gage pairs mounted on opposite sides of the shaft, and oriented at 45 degrees relative to the long axis of the shaft, and 90 degrees relative to each other, measure only the torsional deflections of the shaft.

The basis for operation of the acceleration measurement data acquisition portion of the invention is the direct linear relationship between an acceleration and a transmitted force as described by Newton's Second Law. Uni-axial accelerometers are used to measure impact force induced accelerations. An orthogonal arrangement of three accelerometers measures the accelerations in the three perpendicular directions. If the accelerometer unit is mounted directly on the shaft, then measured accelerations are an indication of the impact induced transmitted forces, i.e., the forces the golfer feels at the club handle. If the accelerometer unit is mounted on the rigid torsion bar which is mounted perpendicular to the shaft, then measured accelerations are an indication of the impact induced transmitted torques.

Measuring impact phenomena is difficult because it is short in duration and highly nonlinear. Impact forces can also excite many modes of vibration, and generate a large amount signal noise. Redundant strain gages, variable accelerometer placements, and adjustable height impacting ball allows for fine tuning of data acquisition parameters to yield clear and useful data.

The feel of a golf club, and the outcome of a golf shot are strongly dependent upon the mass properties of the club head. Specifically, the forces and torques to swing the club, the energy transfer at impact, the transmitted forces and torques (the feel of the impact to the golfer), and the dynamic behavior of the club which includes shaft deflections and induced vibrations, are all in some way influenced by the club head mass properties.

These mass properties include the club head mass (or weight), the three coordinates of the mass center location, and the six independent components of the inertia tensor. The overall mass (weight) and mass center location are both well understood, and accommodating to a sense of scale. The concept of mass moment of inertia is also generally understood. However, the inertia tensor is less well understood, and there is often a lack of scale of inertia values. These facts were the motivation for the "equivalent inertia ellipsoid" method portion of this disclosure.

The following is a brief discussion of the inertia tensor. The inertial properties of a solid body are completely characterized by the 3×3 inertia tensor which is defined as:

$$\begin{vmatrix} Ixx & Ixy & Ixz \\ Ixy & Iyy & Iyz \\ Ixz & Iyz & Izz \end{vmatrix} \quad (3)$$

The matrix is symmetric yielding six independent inertia quantities. The terms on the main diagonal (Ixx, Iyy, Izz) are the moments of inertia. The off-diagonal terms (Ixy, Ixz, Iyz) are the cross-products of inertia. Together, the elements of the inertia tensor represent the dynamic consequences of the arrangement of the mass of a solid body, a golf club head in this case, and are a measure of the resistance of the body to changes in angular motion.

The values of the inertia tensor elements are functions of both the location and orientation of the coordinate axes to which the tensor is referenced. For each coordinate axes location, a unique orientation exists for which the products of inertia are zero with respect to these axes, referred to as the principal axes. The inertia tensor is said to be "diagonalized" and reduces to the form:

$$\begin{vmatrix} Ix & 0 & 0 \\ 0 & Iy & 0 \\ 0 & 0 & Iz \end{vmatrix} \quad (4)$$

where Ix, Iy, and Iz are the principal moments of inertia of the body, which are computed about the principal axes of inertia. The principal axes of inertia are oriented relative to the original coordinate axes using a body 1-2-3 orientation convention (or X-Y-Z Euler angles). In a body orientation scheme, each rotation takes place about an axis whose, location depends upon the preceding rotations. For body 1-2-3, the order of rotations is about the X-axis, Y-axis, and then Z-axis.

Simply speaking, a solid body subjected to an unbalanced torque about a principal axis will experience a change in the angular motion about that axis that is inversely proportional to the corresponding principal inertia component (assuming no other rotations are occurring). Thus, knowledge of the principal inertias of the solid body is useful in evaluating the dynamic behavior of the body when subjected to unbalanced torques. Unfortunately, it is not possible to visually evaluate or make relative comparisons of golf club head inertia values because of their complex and often unique geometries.

As a method for directly comparing the mass and inertia values of the different club heads, mass and inertia equivalent solid ellipsoids are created for each club head. The equivalent solid ellipsoids provide similar (thus comparable) geometries that are sized to have representative mass and inertia characteristics, i.e. the solid ellipsoids are created so they have the same mass and principal inertia values as the club head they represent. From the inertia tensor data input by the user, the principal inertia values and principal axes are determined using standard methods of mechanics. The club head principal inertia values are equated to the formulas for the principal inertias of a solid ellipsoid as given in the following equations:

$$Ix = 4m(pi)abc(a^2+b^2)/15 \quad (5)$$

$$Iy = 4m(pi)abc(a^2+c^2)/15 \quad (6)$$

$$Iz = 4m(pi)abc(b^2+c^2)/15 \quad (7)$$

where a, b, and c represent the semi axes of the ellipsoid, m is the mass of the club head, and Ix, Iy, and Iz are the principal inertias of the club head. Equations (5), (6), and (7) are solved for the semi axes values thus yielding sufficient information to plot the mass and inertia equivalent ellipsoid. The mass center of the ellipsoid is placed coincident to the mass center of the club head, and oriented in the principal inertia directions. Because the ellipsoid has the same inertias as the club head about the principal axes, it will respond similarly to a torque in any of the principal directions. Thus, the ellipsoids can be used to compare the relative merits of different club head designs for such dynamic behavior as torque required to swing reaction to impact, and club head deflections.

As an example that details the procedure for using the device and method, and illustrates the merits of the invention in comparing different club head designs, several unique 5-iron club heads were analyzed with this device and method. The first step in the procedure is determining the mass properties of the golf club heads. In this case, solid modeling was used with the following results:

TABLE 1

Club Head Weight and Mass Center Location

| CLUB HEAD TYPE | WEIGHT (lbs) | X-CG Coord (in) | Y-CG Coord (in) | Z-CG Coord (in) |
|---|---|---|---|---|
| BLADE | 0.488 | 2.849 | −0.271 | 1.451 |
| TBW1 | 0.550 | 3.392 | −0.282 | 1.498 |
| TBW2 | 0.519 | 2.515 | −0.329 | 1.563 |
| TBW3 | 0.493 | 2.531 | −0.304 | 1.470 |
| PW | 0.576 | 3.076 | −0.293 | 1.572 |
| BBW | 0.522 | 3.101 | −0.319 | 1.404 |

TABLE 2

Club Head Principal Inertias and Orientations

| CLUB HEAD | Ix (in-lb-s*s) | Iy (in-lb-s*s) | Iz (in-lb-s*s) | Theta X (deg) | Theta Y (deg) | Theta Z (deg) |
|---|---|---|---|---|---|---|
| BLADE | 0.828 | 0.942 | 0.139 | 8.05 | 34.07 | 9.31 |
| TBW1 | 0.912 | 0.988 | 0.106 | 8.58 | 35.10 | 5.04 |
| TBW2 | 0.668 | 0.653 | 0.021 | 9.04 | 22.53 | −37.17 |
| TBW3 | 0.558 | 0.613 | 0.088 | 7.80 | 31.20 | −3.15 |
| PW | 1.093 | 1.113 | 0.046 | 8.71 | 32.22 | 15.14 |
| BBW | 0.711 | 0.602 | 0.072 | 9.74 | 24.46 | 8.53 |

The data contained in Tables 1 and 2 and the graphical models of the club heads were entered into the system computer. From the mass and inertia data, Equations (3) through (5) were used to determine the equivalent inertia ellipsoids. The resulting ellipsoids were superimposed upon the graphical images of the 5-iron club heads with coincident mass center locations and principal axes orientations as shown in FIGS. 6a through 6f Visual analysis of the figures quickly, clearly, and directly illustrate the differences in club head inertias, which is not possible through visual inspection of the club head geometries alone. For example, it can be seen that club heads with similar mass and mass center location, have large variations in the principal inertias and smaller variations in the principal directions based upon their back weighting schemes (perimeter weighed, bottom weighted, etc.) and material distribution.

Next each club head was mounted to the end of the instrumented shaft for impact testing using the universal mounting hardware. The location was determined for different types of impact (central, outside CG, below CG, etc.) from the mass center location data, and the club head graphical images. The impacting ball guide tube was adjusted accordingly to deliver the ball at the desired impact location. Impact ball height was set based upon the desired amplitude of the data acquisition signals (ball height remains constant for all trials). The, accelerometer triad was located based upon the acceleration directions to be measured. The strain gage and accelerometer signals were zeroed prior to running each trial.

For these 5-iron club heads, three impact cases were studied, central impact (at club head mass center), impact below the mass center, and impact outside mass center (toward club head toe). Several trials were run for each club head and the results compared to computer models (see FIGS. 7 through 10). An analysis of central impact found that the inertia tensor values had no effect on the golfer or golf club. However, for an eccentric impact, the inertia tensor values had a major effect on the forces and torques transmitted back to the golfer (FIGS. 7 and 8), and a moderate effect on the club head deflections' (FIGS. 9 and 10). For an eccentric impact outside the club head CG, the principal inertia component Ix had the greatest effect on the transmitted torques and club head deflections (FIGS. 8 and 10). For an eccentric impact below the CG, the Iz principal inertia component had the greatest effect on the transmitted forces and club head deflections (FIGS. 7 and 9). These relationships between the principal inertia tensor components, the feel of the impact, and the deflections of the club head were verified as shown in FIGS. 7 through 10.

Based upon the findings of this sample study, it is clear that club head inertia markedly affects the golfer and the golf club. However, judging which club head is superior based upon the results is difficult since the what constitutes superior performance is based upon the individual preferences of the golfer. If the golfer prefers lower interactive effects due to impact, club heads with high inertia values perform the best. This criteria may apply to the less expert golfer who may have difficulty in consistently impacting the ball at the club head mass center. Based upon this criteria, the PW (perimeter weighted) club head performs the best to eccentric impacts outside the CG and the simple BLADE club head is superior for eccentric impacts below the CG. The most consistent performance is achieved by the TBW1 (toe and bottom weighted) club head which is second best in both categories of eccentric impacts. If on the other hand, control and feel are preferred by the golfer, then club heads with lower inertia values are desirable. This criteria may apply to the more expert golfer who more consistently impacts the ball at the club head mass center. Based upon this criteria, the TBW2 and TBW3 club heads may be more appropriate. Each golfer must determine what is the ideal combination of club head inertia values for him or her based upon individual preference, feel, and experience, similar to how a golfer chooses the proper club length, shaft flexibility, and swing weight.

The results suggest that designing golf club heads to specific inertia values as opposed to simply manipulating the values in a qualitative manner as is presently done has merit. For example, it may be desirable to select inertia values to give more consistent impact performance in all directions, i.e., more spherical inertia ellipsoids. Also, club head inertia values could be matched (same size ellipsoids) or somehow related in a set of clubs to provide uniform performance from club to club, similar to what is done for club head mass through swing weight matching. At the very least, information concerning the inertia properties of the club head should be provided to the golfer (possibly in the form of inertia ellipsoids) when selecting equipment because of their important effects on the golf swing and shot.

What is claimed is:

1. A method for evaluating and comparing golf club heads based upon mass properties comprising the steps of creating a graphical model of a golf club head, determining the mass, three linear coordinates of the mass center location, and the six elements of the inertia tensor, determining the principal inertia values and principal inertia orientations from said six elements of the inertia tensor, configuring a solid ellipsoid such that it has the same said mass and same said principal inertia values as the golf club head, creating a graphical model of said solid ellipsoid, superimposing said graphical model of the solid ellipsoid over said graphical model of the golf club head such that the solid ellipsoid and the golf club head have coincident mass center locations and principal inertia orientations, generating multiple graphical views of said superimposed image, providing simultaneous graphical images of various golf club heads with respective superimposed solid ellipsoid so to compare the relative size, shape, and orientation of respective solid ellipsoids.

* * * * *